(12) United States Patent
Tomazi

(10) Patent No.: US 8,629,301 B2
(45) Date of Patent: Jan. 14, 2014

(54) PROCESS FOR THE PURIFICATION OF BENZPHETAMINE HYDROCHLORIDE

(75) Inventor: Keith G. Tomazi, Florissant, MO (US)

(73) Assignee: Mallinckrodt LLC, Hazelwood, MO (US)

(*) Notice: Subject to any disclaimer, the term of this patent is extended or adjusted under 35 U.S.C. 154(b) by 1052 days.

(21) Appl. No.: 11/718,989

(22) PCT Filed: Nov. 2, 2005

(86) PCT No.: PCT/US2005/039468
§ 371 (c)(1),
(2), (4) Date: May 10, 2007

(87) PCT Pub. No.: WO2006/057778
PCT Pub. Date: Jun. 1, 2006

(65) Prior Publication Data
US 2009/0124833 A1    May 14, 2009

Related U.S. Application Data

(60) Provisional application No. 60/630,008, filed on Nov. 22, 2004.

(51) Int. Cl.
| C07C 211/00 | (2006.01) |
| C07C 241/00 | (2006.01) |
| C07C 243/00 | (2006.01) |
| C07C 249/00 | (2006.01) |
| C07C 251/00 | (2006.01) |
| C09B 11/02 | (2006.01) |

(52) U.S. Cl.
USPC ............ 564/323; 564/305; 564/314; 564/321

(58) Field of Classification Search
None
See application file for complete search history.

(56) References Cited

U.S. PATENT DOCUMENTS

| 2,789,138 A | 4/1957 | Zeinzelman et al. |
| 3,400,129 A * | 9/1968 | Cour et al. ............ 544/351 |
| 3,911,016 A | 10/1975 | Klinger et al. |
| 4,056,468 A | 11/1977 | Breiter et al. |
| 5,236,922 A | 8/1993 | Lafon |
| 5,618,824 A | 4/1997 | Schmidt et al. |
| 5,976,812 A | 11/1999 | Huber et al. |
| 6,489,343 B2 | 12/2002 | Castro Pineiro et al. |
| 6,518,273 B1 | 2/2003 | Chapman et al. |

OTHER PUBLICATIONS

Pawliszyn, J. Solid Phase Microextraction: Theory and Practice, 1997, p. 130.*
Acs, et al., Enantiomer separation via diastereoisomeric salt formation and liquid-liquid phase transition, ACH Models in Chemistry, vol. 3, No. 132, 1995, pp. 475-478 XP008061978.
Croce et al., A Simple Procedure for N-Propenylation and N-Propynylation of Secondary Amines, Gazzetta Chimica Italiana, 126, 1996, pp. 107-109, XP008061979.
Morrison et al., $\alpha\beta$-Unsaturated Carbonyl Compounds, Organic Chemistry, $3^{rd}$ Edition, 1973, Ch. 28, p. 729.

* cited by examiner

*Primary Examiner* — Clinton Brooks

(57) ABSTRACT

The present invention relates to the economical and separation of benzphetamine hydrochloride and methamphetamine by liquid extraction. An extraction process employing a suitable organic solvent and water at a pH in the range of from about 6 to about 8 provides excellent removal of the methamphetamine by dissolution in the water phase while the benzphetamine dissolves in the organic phase. Simple separation of the two phases results in separation of the two amines.

33 Claims, No Drawings

PROCESS FOR THE PURIFICATION OF BENZPHETAMINE HYDROCHLORIDE

CROSS REFERENCE TO RELATED APPLICATIONS

This application is a national stage application of PCT/US2005/039468, filed Nov. 2, 2005, which claims the benefit of U.S. Provisional Application No. 60/630,008 filed Nov. 22, 2004.

BACKGROUND OF THE INVENTION

This invention relates to a process for removal of methamphetamine from benzphetamine hydrochloride thereby providing highly pure benzphetamine hydrochloride by means of a convenient liquid extraction process employing an organic solvent and water.

The production of benzphetamine has been known for a considerable period of time and was disclosed in U.S. Pat. No. 2,789,138 to Heinzelman et al. The chemical name of the physioacitve material, benzphetamine, is d-N-methyl-N-benzyl-beta-phenylisopropylamine. According to that patent benzyl chloride is reacted with methamphetamine in the presence of a base, typically sodium carbonate. The reaction is typically carried out in a non-reactive organic solvent such as benzene, toluene, xylene or the like. The product is recovered by mixing the reaction mixture with water, extracting with solvent, then converting the benzphetamine to the hydrochloride by addition of hydrochloric acid. The thus produced acid salt is then fractionally distilled under vacuum at temperatures in the range of from about 155° C. to about 165° C. to obtain the amine. Such purification process has several disadvantages including the exposure of the product to high temperatures, and the need for expensive vacuum pumps and a vacuum still to achieve the desired reduced pressure.

The impurity of most concern in the process for preparing benzphetamine hydrochloride is methamphetamine. It is self-evident that any pharmaceutical should be as pure as possible and that such a drug as methamphetamine be eliminated to the extent economically feasible.

Extraction of methamphetamine has been the subject of research in the prior art. An activated methamphetamine is shown in U.S. Pat. No. 5,976,812. The activated methamphetamine is in a class of derivatives of very active materials, typically methamphetamine-p-carboxybutyl-maleinimidoethylamide. In the purification process for this type of compound, the derivative is shaken with sodium hydroxide in water forming oil which is extracted three times with toluene. U.S. Pat. No. 4,056,922 discloses that methamphetamine can be extracted at either pH 2 or pH 9 with concentrating agent selected from silica gel and kieslguhr.

While there are numerous purification schemes available on an analytical basis to remove materials such as methamphetamine, a convenient large-scale production method to provide highly pure benzphetamine hydrochloride substantially free of methamphetamine is not commercially available other than by vacuum distillation. A convenient, large-scale method to provide benzphetamine hydrochloride has not been heretofore available.

BRIEF DESCRIPTION OF THE INVENTION

In accordance with this invention there is provided a novel, efficient and large-scale method for separating methamphetamine from benzphetamine hydrochloride. As noted above, the reaction product of benzyl chloride and methamphetamine is typically acidified to provide benzphetamine hydrochloride. It is inevitable that some amount of methamphetamine is found in the benzphetamine hydrochloride product. There has now been discovered a convenient yet effective liquid extraction method for removing methamphetamine from benzphetamine hydrochloride.

More particularly, it has been discovered that in a narrow pH range of from about 6.0 to about 8.0 there is a high degree of separation of the two amines between an organic phase and an aqueous phase such that the tertiary amine, benzphetamine hydrochloride is converted to the base that partitions into the organic phase while the secondary amine, methamphetamine hydrochloride, is not converted to its base and thus partitions into the aqueous phase. More particularly, in a pH range of from about 6 to about 6.5 there is nearly complete separation of the amines between the organic phase and the aqueous phase. At such pH range, benzphetamine base is conveniently recovered from the organic phase by separating the organic phase from the aqueous phase. The organic phase is then treated with an acid, typically hydrochloric acid, typically providing a pH that converts the benzphetamine base into the acid salt, typically the hydrochloride salt. Such pH to convert the base to the acid salt is typically below about 4 and more preferably about 1. As is well known, the hydrochloride salt is not soluble in the organic phase and can be recovered by any suitable means. As is known in the prior art, the benzphetamine base is typically an oil at room temperature and can be distilled out under vacuum.

DETAILED DESCRIPTION OF THE INVENTION

The present method utilizes the control of the pH of the system so as to take advantage of the difference in the basicity constants, $K_b$, between benzphetamine hydrochloride and methamphetamine. Both amines in the process of this invention are weak bases. Benzphetamine is a tertiary amine, and methamphetamine is a secondary amine. The literature indicates that secondary and tertiary amines differ in $K_b$ by a factor of 2. However, it has been discovered that the difference between a benzyl amine (benzphetamine) and a methyl amine (methamphetamine) is quite large. That is, the $K_b$ of benzphetamine is about $\frac{1}{20}^{th}$ of the $K_b$ of methamphetamine. It has further been discovered that concentration of benzphetamine in an organic solvent is approximately 70 to 700 times greater than its solubility in water. Thus a nearly complete separation of benzphetamine can be accomplished by solvent extraction because methamphetamine hydrochloride does not partition in the organic solvent such as toluene.

In accordance with this invention, crude benzphetamine hydrochloride is added to a vessel containing both an organic solvent and water. While stirring vigorously, the pH of the water phase is adjusted to the range of from about 6.0 to about 8.0 by the addition of a suitable acid or base. At such pH range the benzphetamine hydrochloride is converted to a base, and methamphetamine is converted to an acid salt. Vigorous agitation of the mixture assures adequate contact of both phases with the crude benzphetamine base containing methamphetamine contaminant. Upon contact, the benzphetamine partitions into the organic phase and the methamphetamine hydrochloride partitions into the aqueous phase. This operation is performed at ambient temperature and pressure. The only equipment required is a suitable vessel and an adequate stirrer. Optionally, the process of this invention can be carried out in the reactor in which the benzphetamine hydrochloride is produced.

Alternatively, this process works in the opposite direction. A mixture of methamphetamine base and benzphetamine base that is dissolved in an organic solvent may be added to water, and while stirring, the pH may be adjusted to the range of from about 6.0 to about 8.0 with a suitable acid or base. The benzphetamine base remains in the organic phase, while methamphetamine hydrochloride partitions into the aqueous phase.

Any number of organic solvents can be employed in the process of this invention. Such solvent must be non-reactive and have sufficient solubility for benzphetamine hydrochloride. Typical organic solvents include aromatic solvents such as benzene, toluene, xylene, and the like; or aliphatic or cyclic aliphatic solvents such as hexane, heptane, cyclohexane, and the like. A preferred organic solvent for the organic phase in the process of this invention is toluene because it is inert to benzphetamine base and has sufficient solvent ability toward the base.

Typically, the pH of the aqueous phase is adjusted with a base because the hydrochloride salt provides a low pH. Any number of bases can be employed provided such base does not react with the amines in the mixture and should be stronger bases than either of the amines. Such bases include sodium carbonate, alkali metal hydroxides such as sodium hydroxide, potassium hydroxide and the like, alkali metal carbonates and alkali metal bicarbonates such as sodium carbonate or bicarbonate, potassium carbonate or bicarbonate and the like.

Usually, the aqueous phase is rendered acid by the addition of the acid salt, benzphetamine hydrochloride. However, should the pH of the aqueous phase require lowering, any number of acids may be added to lower the pH to the required range. Typically, hydrochloric acid would be added to the aqueous phase to lower the pH as it does not provide any additional elements to the process than is necessarily present. Other acids that could be employed include mineral acids such as sulfuric acid, phosphoric acid, at the like; and organic acids such as acetic acid and the like.

The volume of the organic phase and the aqueous phase is typically equal in the vessel employed in the process of this invention. Equal ratios are not necessary, however, and the organic phase to aqueous phase ratio may be between 1:3 and 3:1; preferable between 1:2 and 2:1, and more preferably 1:1.

After the crude benzphetamine hydrochloride is extracted with the organic solvent and water at a pH in the range of from about 6 to about 8, benzphetamine is in the organic phase, and methamphetamine is in the aqueous phase. The aqueous and organic phases are separated, and benzphetamine hydrochloride may be extracted from the organic phase using, for example, hydrochloric acid. The application of heat to the organic phase may be used to dehydrate the organic phase using distillation, which is more fully described in co-pending U.S. Prov. Appl. entitled "Crystallization Method for Benzphetamine" filed concurrently herewith the same obligations for assignment.

Preferred Embodiments

EXAMPLE 1

To a suitable flask containing 50 ml of deionized water there were added 4 g of crude benzphetamine hydrochloride, having a tan color, and 50 ml of toluene. With vigorous stirring, the pH of the aqueous phase was adjusted to 6.30 with sodium carbonate aqueous solution. The contents of the flask was transferred to a separatory funnel and allowed to settle into two phases. The aqueous layer was decanted. The toluene remaining in the funnel was washed with 25 ml of deionized water and 1.02 equivalents of 37% hydrochloric acid were added. The contents of the funnel were mixed thoroughly by vigorous shaking. The pH of aqueous layer was measured with a paper test strip followed by the addition of a few more drops of hydrochloric acid to bring the pH of the aqueous layer to a range of 0-1. The toluene/acid mixture was transferred to a distillation apparatus consisting of a suitable still, a heating mantle, a magnetic stirrer, a reflux condenser and a Dean Stark trap. After water was collected as a distillate, the apparatus was cooled. The contents of still remained liquid (no solids formed) and a layer of benzphetamine hydrochloride formed. The aqueous layer was drained from the Dean Stark trap and the toluene layer was returned to the still. Upon subsequent heating to the boiling point, the solids dissolved or melted and as distillation continued, sufficient precipitate formed to stop the magnetic stirrer. The toluene/benzphetamine hydrochloride mixture was cooled to room temperature, filtered and washed with additional toluene. There was collected 2.76 g of purified benzphetamine hydrochloride having a white appearance. Analytical analysis, by means of HPLC, of several aspects of the above experiment appear in Table 1 below.

TABLE 1

| Description | Benzphetamine HCl Mass (g) | Methamphetamine Area % | Benzphetamine HCl Area % |
| --- | --- | --- | --- |
| Crude Benzphetamine | 4.00 | 6.10 | 87.17 |
| Aqueous Extract | 0.05 | 67.06 | 20.63 |
| Aqueous Wash | 0.001 | 18.31 | 29.28 |
| Toluene Extract | 3.307 | 0.00 | 94.19 |
| Filtrate | 0.260 | 0.07 | 76.64 |
| Benzphetamine Hydrochloride Product | 2.76 | 0.00 | 98.12 |

The overall yield of product in the above procedure was 83%, while the yield through the extraction is 97.8%. There was no detectable methamphetamine in the recrystallized product, and only traces of benzphetamine in the aqueous layer. The above described procedure demonstrates the liquid partitioning of benzphetamine hydrochloride from methamphetamine in high yield and improved color.

The partition coefficients for benzphetamine and methamphetamine are presented in Table 2 below. The partition coefficient is defined as the ratio of the equilibrium concentration of the specie in the organic layer to the equilibrium concentration of the specie in the aqueous layer.

TABLE 2

| pH | Benzphetamine | Methamphetamine |
| --- | --- | --- |
| 4 | 0.600 | 0.015 |
| 6 | 73.657 | 0.000 |
| 8 | ∞ | 0.124 |
| 10 | ∞ | 3.366 |

As indicated by the data in Table 2 above, the partition coefficient at pH 6 is highly favorable for maximum separation of the species.

While this invention has been described with respect to various specific examples and embodiments, it is to be understood that the invention is not limited thereto.

What is claimed is:

1. A process for removing methamphetamine hydrochloride from crude benzphetamine hydrochloride which comprises subjecting the said crude hydrochlorides to liquid extraction with an organic solvent and water at a pH in the range of from about 6 to 8 wherein the benzphetamine hydrochloride is converted to a base and separates into the organic phase and the methamphetamine hydrochloride remains in the aqueous phase.

2. The process of claim 1 wherein the pH is in the range of from about 6 to about 6.5.

3. The process of claim 1 wherein the organic solvent selected from the group consisting of benzene, toluene, xylene, hexane, heptane, cyclohexane.

4. The process of claim 3 wherein organic solvent is toluene.

5. The process of claim 1 wherein the pH of the water is adjusted with an acid.

6. The process of claim 5 wherein the acid is selected from the group consisting of hydrochloric acid, sulfuric acid, phosphoric acid, and acetic acid.

7. The process of claim 6 wherein the acid is hydrochloric acid.

8. The process of claim 1 wherein the pH of the water is adjusted with a base.

9. The process of claim 8 wherein the base is selected from the group consisting of alkali metal carbonates, alkali metal bicarbonates and alkali metal hydroxides.

10. The process of claim 9 wherein the base is sodium carbonate.

11. A process for removing methamphetamine from crude benzphetamine hydrochloride which comprises the steps of:
   A. subjecting the crude benzphetamine hydrochloride to liquid extraction with an organic solvent and water at a pH in the range of from about 6 to 8;
   B. separating the water containing the methamphetamine base from the organic solvent containing benzphetamine base, then converting the benzphetamine base to the hydrochloride salt; and
   C. separating the benzphetamine hydrochloride salt from the organic solvent.

12. The process of claim 11 wherein step C is performed by filtration of the benzphetamine hydrochloride salt from the organic solvent.

13. The process of claim 11 wherein step C is performed by extracting benzphetamine hydrochloride salt from the organic solvent.

14. The process of claim 11 wherein the pH of the water in step A is in the range of from about 6 to about 6.5.

15. The process of claim 11 wherein the organic solvent selected from the group consisting of benzene, toluene, xylene, heptane and cyclohexane.

16. The process of claim 15 wherein organic solvent is toluene.

17. The process of claim 11 wherein the pH of the water is adjusted with an acid.

18. The process of claim 17 wherein the acid is selected from the group consisting of hydrochloric acid, sulfuric acid, phosphoric acid and acetic acid.

19. The process of claim 18 wherein the acid is hydrochloric acid.

20. The process of claim 11 wherein the pH of the water is adjusted with a base.

21. The process of claim 20 wherein the base is selected from the group consisting of alkali metal hydroxides, alkali metal carbonates and alkali metal bicarbonates.

22. The process of claim 21 wherein the base is selected from the group consisting of sodium hydroxide, potassium hydroxide; sodium carbonate, potassium carbonate, sodium bicarbonate, potassium bicarbonate.

23. The process of claim 22 wherein the base is sodium carbonate.

24. A process for removing methamphetamine hydrochloride from crude benzphetamine base which comprises subjecting crude methamphetamine base and the benzphetamine base to liquid extraction with an organic solvent and water at a pH in the range of from about 6 to 8 wherein the benzphetamine base remains in the organic phase and the methamphetamine is converted to a salt and remains in the aqueous phase.

25. The process of claim 24 wherein the pH is in the range of from about 6 to about 6.5.

26. The process of claim 24 wherein the organic solvent selected from the group consisting of benzene, toluene, xylene, hexane, heptane, cyclohexane.

27. The process of claim 26 wherein organic solvent is toluene.

28. The process of claim 24 wherein the pH of the water is adjusted with an acid.

29. The process of claim 28 wherein the acid is selected from the group consisting of hydrochloric acid, sulfuric acid, phosphoric acid, and acetic acid.

30. The process of claim 29 wherein the acid is hydrochloric acid.

31. The process of claim 24 wherein the pH of the water is adjusted with a base.

32. The process of claim 31 wherein the base is selected from the group consisting of alkali metal carbonates, alkali metal bicarbonates and alkali metal hydroxides.

33. The process of claim 32 wherein the base is sodium carbonate.

* * * * *